(12) United States Patent
Wang et al.

(10) Patent No.: US 7,990,527 B2
(45) Date of Patent: *Aug. 2, 2011

(54) REFRACTIVE-INDEX SENSOR

(75) Inventors: Xiao-Ling Wang, Beijing (CN); Guo-Fan Jin, Beijing (CN); Zhen-Feng Xu, Beijing (CN); Jun Zhu, Beijing (CN)

(73) Assignees: Tsinghua University, Beijing (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 232 days.

This patent is subject to a terminal disclaimer.

(21) Appl. No.: 12/143,660

(22) Filed: Jun. 20, 2008

(65) Prior Publication Data

US 2009/0153843 A1    Jun. 18, 2009

(30) Foreign Application Priority Data

Dec. 12, 2007    (CN) .......................... 2007 1 0125108

(51) Int. Cl.
*G01N 21/41*    (2006.01)

(52) U.S. Cl. ........ 356/128; 385/125; 385/129; 385/130; 385/131

(58) Field of Classification Search .................. 356/128; 385/125, 129–131
See application file for complete search history.

(56) References Cited

U.S. PATENT DOCUMENTS

| | | | |
|---|---|---|---|
| 6,058,127 A * | 5/2000 | Joannopoulos et al. ........ 372/92 |
| 6,198,860 B1 * | 3/2001 | Johnson et al. ................. 385/28 |
| 6,643,439 B2 * | 11/2003 | Notomi et al. ................ 385/125 |
| 6,683,898 B2 * | 1/2004 | Østergaard et al. ........ 372/43.01 |
| 6,697,542 B2 * | 2/2004 | Platzman et al. .................. 385/5 |
| 6,873,777 B2 * | 3/2005 | Bourelle ........................ 385/129 |
| 6,879,766 B2 * | 4/2005 | Tomaru ......................... 385/129 |
| 6,912,334 B2 * | 6/2005 | Koyama .......................... 385/16 |
| 7,200,312 B2 * | 4/2007 | Furuya et al. ................. 385/129 |
| 7,242,837 B2 * | 7/2007 | Talneau et al. ................ 385/129 |
| 7,440,658 B2 * | 10/2008 | Furuya et al. .................... 385/39 |
| 2002/0048422 A1 * | 4/2002 | Cotteverte et al. ................ 385/4 |
| 2005/0146778 A1 * | 7/2005 | Noda et al. .................... 359/321 |
| 2006/0204161 A1 * | 9/2006 | Noda et al. ........................ 385/1 |
| 2007/0252981 A1 | 11/2007 | Spillane et al. |

OTHER PUBLICATIONS

Channel drop filters in photonic crystals, Optics Express, Shanhui Fan et al. vol. 3, No. 1.

* cited by examiner

*Primary Examiner* — Tarifur R Chowdhury
*Assistant Examiner* — Isiaka O Akanbi
(74) *Attorney, Agent, or Firm* — D. Austin Bonderer

(57) ABSTRACT

An exemplary refractive-index sensor includes a photonic crystal microcavity structure, a light source, and a detector. The photonic crystal microcavity structure includes a photonic crystal layer having first holes and a second hole defined therein. The first holes are arranged in a regular pattern of staggered parallel rows. The second hole is at an approximate center of the regular pattern, instead of a first hole. A diameter of the second hole is different from that of the first holes. The first holes at each of opposite ends of the row having the second hole are omitted, thereby defining an input waveguide and an output waveguide. The light source is adjacent to the input waveguide. The detector is adjacent to the output waveguide.

8 Claims, 5 Drawing Sheets

REFRACTIVE-INDEX SENSOR

BACKGROUND OF THE INVENTION

1. Field of the Invention

The invention relates to refractive-index sensors and, particularly, to a refractive-index sensor based on photonic crystals.

2. Description of Related Art

Recently, there has been interest in using photonic crystals to measure refractive index change for sensing applications, because of the unique light-confinement mechanism provided by the photonic bandgap. Photonic crystals provide the potential for a high quality factor (high-Q) microcavity and a small sensing area. For example, the sensing area may be 10☐ $\mu m^2$, which requires only a very small amount (e.g., $10^{-15}$ liters) of sample. These advantages make the photonic crystal an attractive candidate for use in measuring small samples. Thus, the refractive-index sensor based on photonic crystals has been developed extensively.

A conventional refractive-index sensor based on photonic crystals that is capable of detecting a change in refractive index of 0.2 has been proposed. However, the resolution of the refractive-index sensor is limited. In addition, another conventional refractive-index sensor with a two-dimensional photonic crystal microcavity has been proposed. The refractive-index sensor can measure a sample having a refractive index (n) within a range from n=1.0 to n=1.5. However, the refractive-index sensor has low light transmission. The refractive-index sensor also has drawbacks such as low sensitivity and low accuracy of measurement.

What is needed, therefore, is a refractive-index sensor having high light transmission and improved accuracy of measurement as well as improved sensitivity.

SUMMARY OF THE INVENTION

In one aspect, a refractive-index sensor includes a photonic crystal microcavity structure, a light source, and a detector. The photonic crystal microcavity structure includes a photonic crystal layer. The photonic crystal layer has a plurality of first holes and at least one second hole defined therein. The first holes are arranged in a regular pattern of staggered parallel rows in the photonic crystal layer. A diameter of the second holes is different from a diameter of the first hole and is located at an approximate center point of the middle row of the regular pattern instead of a first hole. A plurality of the first holes at each of opposite ends of a row having the second hole are omitted to define an input waveguide and an output waveguide. The light source is disposed adjacent to the input waveguide. The detector is disposed adjacent to the output waveguide.

In another aspect, a refractive-index sensor includes a photonic crystal microcavity structure, a light source, and a detector. The photonic crystal microcavity structure includes a photonic crystal layer. The photonic crystal layer has a plurality of first holes and at least one second hole defined therein. The first holes are arranged in a regular pattern of first staggered parallel rows, a middle row, and a regular pattern of second staggered parallel rows in the photonic crystal layer. The middle row is between the first and second staggered parallel rows. The second hole is located at a middle of the middle row of first holes. A diameter of the second hole is large than a diameter of the first holes. The number of first holes at one side of the second hole in the middle row is less than half the number of first holes in any of the other rows thereby defining an input waveguide. The number of first holes at the other side of the second hole in the middle row is less than half the number of first holes in any of the other rows thereby defining an output waveguide. The light source is disposed adjacent to the input waveguide. The detector is disposed adjacent to the output waveguide.

Other novel features and advantages of the present refractive-index sensor will become more apparent from the following detailed description of preferred and exemplary embodiments, when taken in conjunction with the accompanying drawings.

BRIEF DESCRIPTION OF THE DRAWINGS

Many aspects of the present refractive-index sensor can be better understood with reference to the following drawings. The components in the drawings are not necessarily to scale, the emphasis instead being placed upon clearly illustrating the principles of the present refractive-index sensor.

Figure 1:
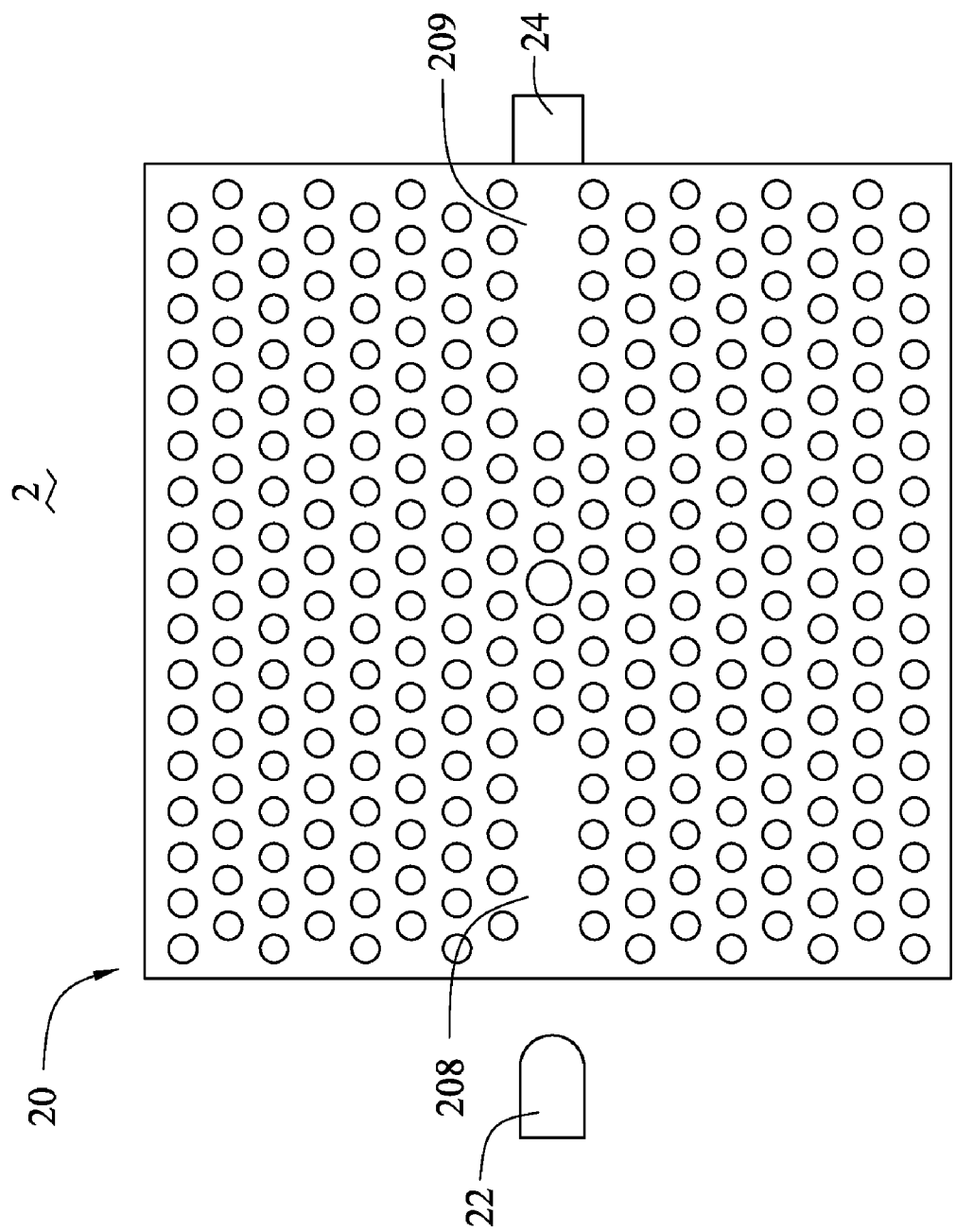
FIG. 1 is a plan view of a refractive-index sensor, in accordance with a present embodiment.

Corresponding reference characters indicate corresponding parts throughout the various views. The exemplifications set out herein illustrate at least one preferred embodiment of the present refractive-index sensor, in one form, and such exemplifications are not to be construed as limiting the scope of the invention in any manner.

DETAILED DESCRIPTION OF THE INVENTION

Reference will now be made to the drawings to describe various embodiments of the present refractive-index sensor, in detail.

Referring to FIG. 1, a refractive-index sensor 2, according to a present embodiment, is shown. The refractive-index sensor 2 includes a photonic crystal microcavity structure 20, a light source 22, and a detector 24.

Figure 2:
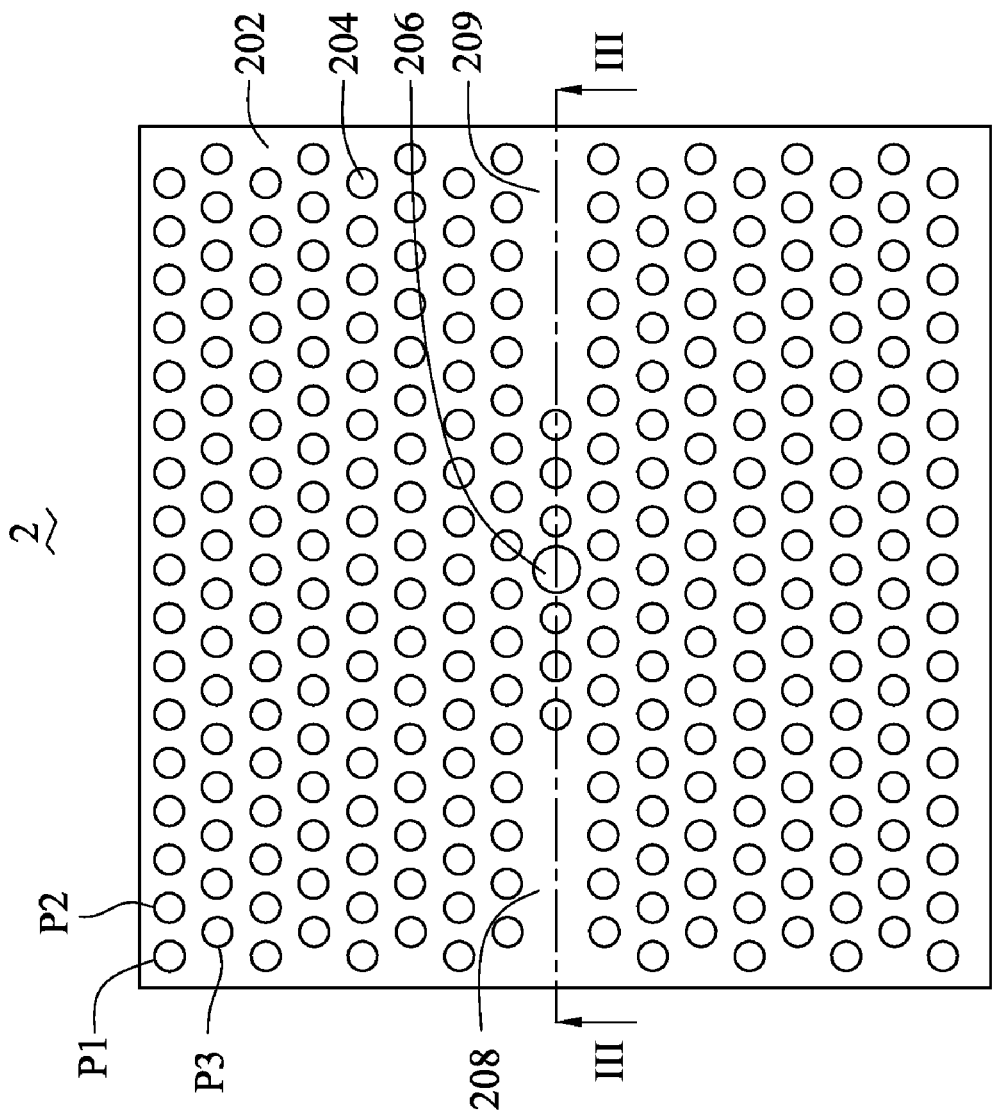
FIG. 2 is a plan view of a photonic crystal microcavity structure of the refractive-index sensor of FIG. 1.
Figure 3:
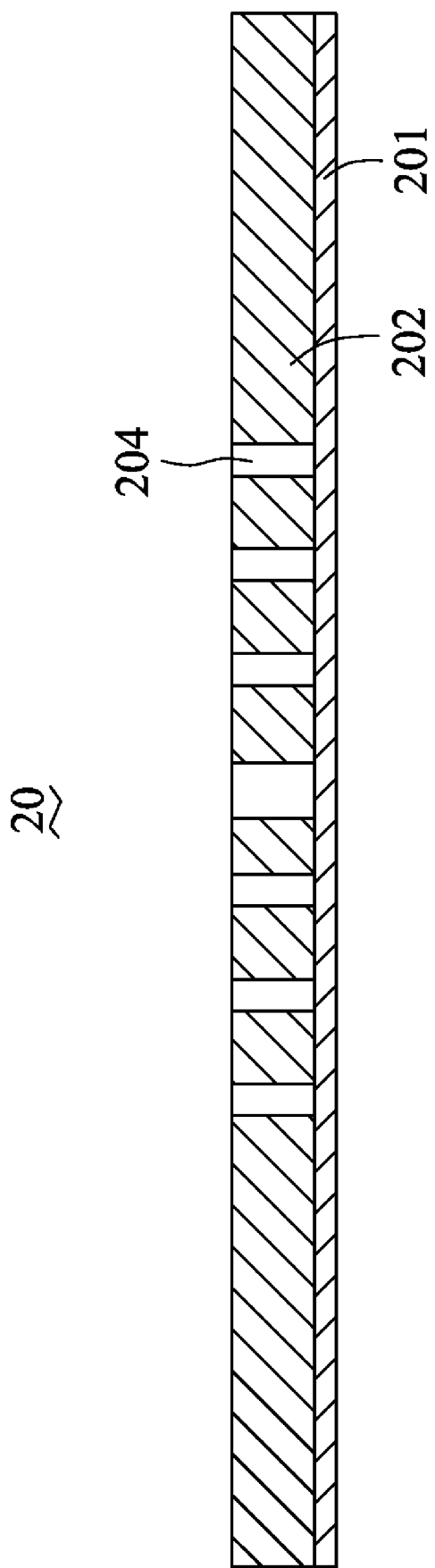
FIG. 3 is a cross-sectional view of the photonic crystal microcavity structure of FIG. 2 taken along a line III-III thereof.

Referring also to FIG. 2 and FIG. 3, the photonic crystal microcavity structure 20 includes a substrate 201 and a photonic crystal layer 202 disposed thereon. A thickness of the photonic crystal layer 202 ranges from 0.4a to 0.7a, where 'a' is a lattice constant. Preferably, the thickness of the photonic crystal layer 202 is 0.6a.

The photonic crystal layer 202 is made of Si (silicon), GaAs (gallium arsenide) or GaAlAs (gallium aluminum arsenate). Suitably, the photonic crystal layer 202 of the present embodiment is made of GaAlAs with a lattice constant of a=440 nm (nanometers). In the present embodiment, the photonic crystal layer 202 is formed on the substrate 201 by a layer epitaxy method. The substrate 201 is made of a material suitable for the growth of the photonic crystal layer 202 by the layer epitaxy method. For example, the substrate 201 can be made of GaAs or GaN (gallium nitride), which are suitable for the growing of a GaAs or GaAlAs photonic crystal layer 202. However, to achieve a silicon photonic crystal layer 202, a $SiO_2$ (silicon dioxide) substrate 201 should be used.

The photonic crystal layer 202 has a plurality of first holes 204 and at least one second hole 206 defined therein. The holes 204, 206 are fabricated by electron-beam lithography or reactive ion etching (RIE). In the present embodiment, the holes 204, 206 are cylindrical. In other embodiments, the holes 204, 206 can be any of various suitable shapes. The first holes 204 are arranged in an array of m rows, each of which has n holes. That is, rows of the first holes 204 are counted from top to bottom as $1^{st}, 2^{nd}, 3^{rd} \ldots$, and $m^{th}$. The first holes 204 in each column are counted from left to right as $1^{st}, 2^{nd}, 3^{rd} \ldots$, and $n^{th}$. Typically, each of m and n is an integer ranging from 14 to 18. In the present embodiment, the first holes 204 are arranged in 17 rows. Each row has 17 first holes 204, except for the middle ($9^{th}$) row, as shown in FIG. 2.

Referring particularly to FIG. 2, the first holes 204 are arranged in a regular pattern of staggered parallel rows in the photonic crystal layer 202. That is, the rows of the first holes 204 are disposed parallel to each other. The first holes 204 in each row are spaced from each other a predefined constant distance. In addition, the first holes 204 in each two adjacent rows are staggered relative to each other. For example, the first holes 204 in the $1^{st}$ row and the first holes 204 in the adjacent $2^{nd}$ row are in an unaligned relationship. Put another way, each of the first holes 204 is arranged so as to be part of a triangular array. For example, the leftmost two first holes 204 in the $1^{st}$ row, i.e. hole $P_1$ and hole $P_2$, and the leftmost hole in the $2^{nd}$ row, i.e. hole $P_3$, when connected by a line form a triangular shape. Preferably, the triangular shape formed is an equilateral triangle.

The second hole 206 is located at the $j^{th}$ hole of the $j^{th}$ row of the array of first holes 204, where i is more than 1 and less than m, and j is more than 1 and less than n. Preferably, i is an integer proximate to the ratio of m/2, and j is an integer proximate to the ratio of n/2. That is, the second hole 206 is located at an exact or approximate center point of the middle row of the pattern, instead of a first hole 204. A diameter of the second hole 206 is different from that of each first hole 204, thereby forming a resonant cavity located at the second hole 206. The diameters of the first holes 204 and the second hole 206 are chosen to allow the photonic crystal microcavity structure 20 to have a desired resonant wavelength. In the present embodiment, a diameter of each of the first holes 204 is in an approximately range from 0.3 a to 0.5 a, while the diameter of the second hole 206 is in an approximately range from 0.05 a to 0.6 a, where a is a lattice constant of the photonic crystal layer 202. Preferably, the diameter of each first hole 204 is 0.36 a, and the diameter of the second hole 206 is 0.55 a.

A plurality of first holes 204 at each of opposite ends of the row having the second hole 206 is omitted. This defect in the pattern defines an input waveguide 208 and an output waveguide 209. In FIG. 2, the input waveguide 208 is formed by omitting some of the first holes 204 at a left end of the row containing the second hole 206, while the output waveguide 209 is formed by omitting some of the first holes 204 at a right end of the row containing the second hole 206. In addition, the input waveguide 208 and the output waveguide 209 are respectively spaced from the second hole 206 by a predetermined number of first holes 204. The number of first holes 204 between the second hole 206 and each of the input waveguide 208 and the output waveguide 209 is in an approximately range from two to five. Suitably, the input waveguide 208 and the output waveguide 209 are each spaced from the second hole 206 by three first holes 204.

Referring to FIG. 1, the light source 22 is disposed adjacent to the input waveguide 208. The light emitted from the light source 22 has a wavelength within the resonant wavelength of the resonant cavity. For example, the emitted light has a wavelength ranging from 1800 nm to 1830 nm. The light source 22 can be a light-emitting diode (LED) or a laser diode.

The detector 24 is disposed adjacent to the output waveguide 209. The light emitted from the light source 22 is guided through the input waveguide 208 and output from the output waveguide 209. The detector 24 is configured to detect the light output from the output waveguide 209. In the present embodiment, because the wavelength of light emitted from the light source 22 is infrared light, the detector 24 is capable of detecting wavelengths within infrared spectral bands. For example, an indium gallium arsenide (InGaAs) infrared detector is selected as the detector 24. Furthermore, the detector 24 can be connected to an external pick-up device so that the measuring results, e.g. output light entering the detector 24, can be monitored.

In use of the refractive-index sensor 2, a sample medium to be tested is filled into the first holes 204 and the second hole 206. The medium may be in liquid, gas or vapor form. When light passes through the resonant cavity, a change in resonant wavelength is observed. In addition, the magnitude of the change in resonant wavelength corresponds to a refractive index of the medium in the second hole 206. For example, uncured silicon resin with a particular refractive index and having a thickness in an approximately range from 200 μm to 500 μm can be disposed on the surface of the photonic crystal microcavity structure 20. Then the silicon resin enters the first holes 204 and second hole 206. Light emitted from the light source 22 is modulated by the resonance effect of the resonant cavity and finally detected by the detector 24.

Figure 4:
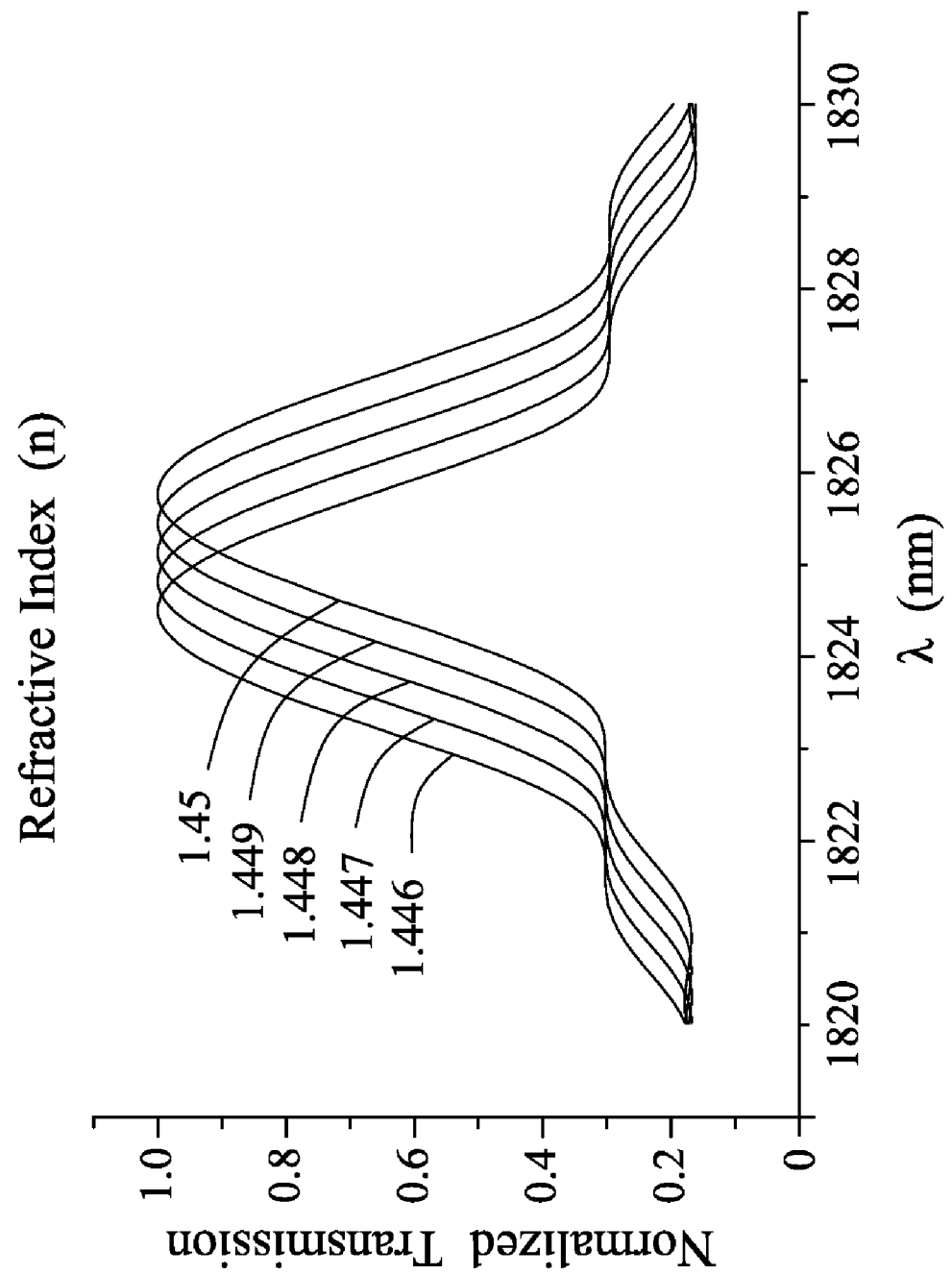
FIG. 4 is a graph showing transmission spectra measured by the refractive-index sensor of FIG. 1.

Referring to FIG. 4, this shows a graph of transmission spectra obtained from samples having different refractive indices. In the present example, the refractive indices of five samples of uncured silicon resin as a medium are plotted. The five samples have refractive indices in a range from 1.446 to 1.450, in 0.001 increments. Thus the change in resonant wavelength of a sample of any substance (whether silicon resin or another substance) having an unknown refractive index can be measured, and a corresponding refractive index of the sample can be obtained accordingly.

Figure 5:
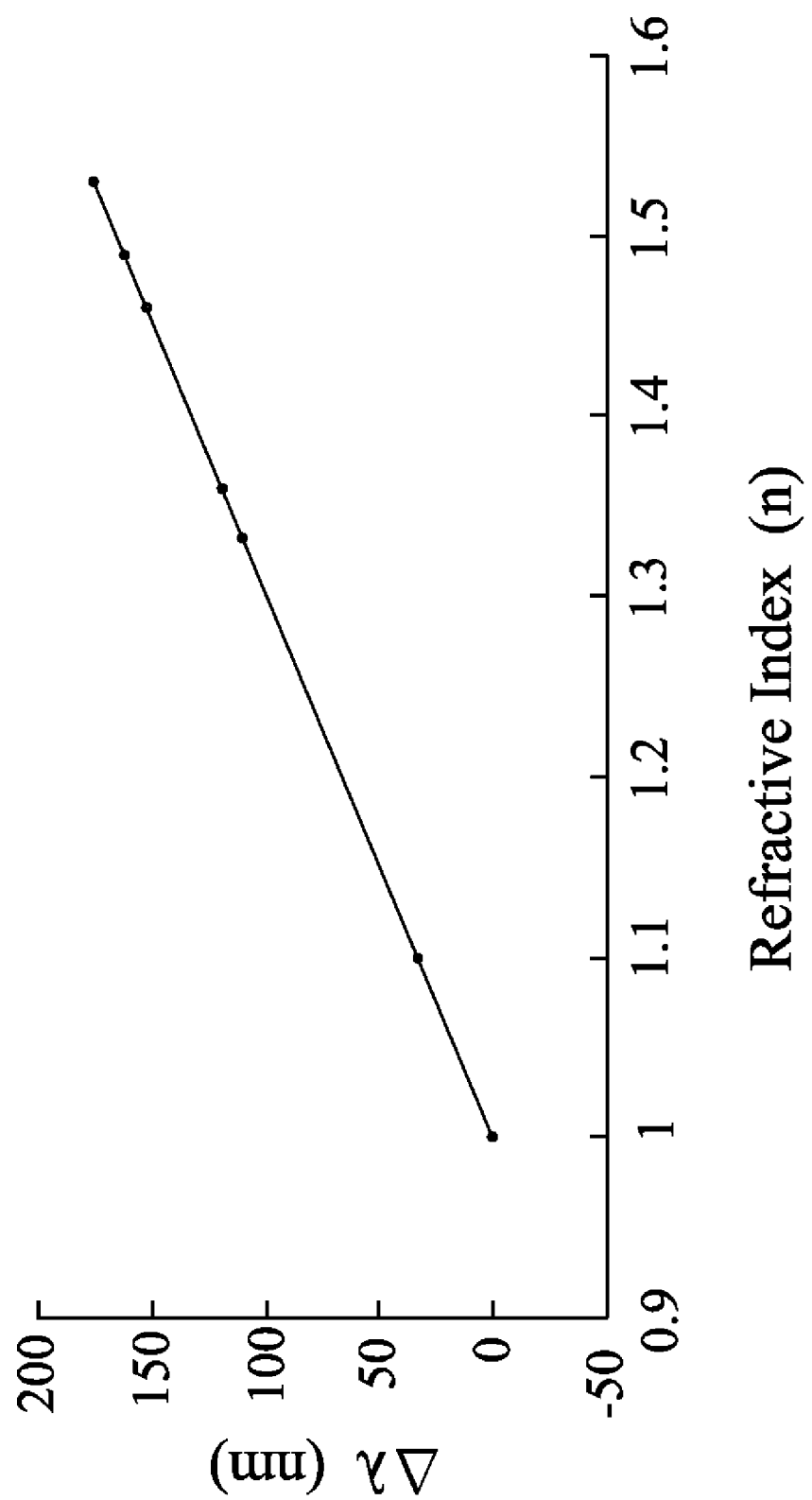
FIG. 5 is a graph showing a correlation between resonant wavelength shifts and refractive indices, in accordance with the present embodiment.

Referring to FIG. 5, this shows resonant wavelength shift Δλ plotted as a function of refractive index (n). It is seen that the resonant wavelength shift Δλ increases with respect to increments in the refractive index. In the present example, the samples taken for measurement include air with a refractive index close to 1, liquid carbon dioxide with a refractive index close to 1.1, water with a refractive index close to 1.333, acetone with a refractive index close to 1.36, absolute alcohol with a refractive index close to 1.46, 80% (by weight) solution of sugar in water with a refractive index close to 1.49, and saturated solution of sodium chloride in water with a refractive index close to 1.53. It is seen that there is a substantially linear relationship between the resonant wavelength shifts Δλ and the refractive indices of the samples. In particular, for each 0.001 increment in the refractive index, the resonant wavelength increases 0.33 nm. Thus, the sensitivity of the detector is 330 nm/RIU (nanometers/refractive index unit).

Parameters such as the diameter of each first hole 204, the diameter of the second hole 206, and dispositions of the first waveguide 208 and the second waveguide 209 are chosen to obtain improved light transmission ranging from 40% to 70%. In addition, the ratio of resonant wavelength shift Δλ to change in refractive index Δn is large (e.g. a sensitivity of 330 nm/RIU). Thus the refractive-index sensor 2 has improved measurement accuracy, and is capable of measuring small changes in refractive index (e.g. Δn=0.001). Furthermore, the range of refractive indices that can be measured by the refractive-index sensor 2 is large. For example, refractive indices ranging from 1.0 to 1.6 can be measured. Therefore, the refractive index of any one of numerous samples can be easily obtained according to the resonant wavelength shift $\Delta\lambda$ thereof.

Finally, it is to be understood that the above-described embodiments are intended to illustrate rather than limit the invention. Variations may be made to the embodiments without departing from the spirit of the invention as claimed. The above-described embodiments illustrate the scope of the invention but do not restrict the scope of the invention.

What is claimed is:

1. A refractive-index sensor, comprising:
   a photonic crystal microcavity structure comprising a photonic crystal layer having a plurality of first holes and at least one second hole defined therein, the first holes being arranged in a regular pattern of first staggered parallel rows, a middle row, and a regular pattern of second staggered parallel rows in the photonic crystal layer, the middle row being between the first and second staggered parallel rows, the at least one second hole being located at a middle of the middle row of first holes, a diameter of the at least one second hole being larger than a diameter of the first holes, the number of first holes at one side of the at least one second hole in the middle row being less than half the number of first holes in any of the other rows thereby defining an input waveguide, and the number of first holes at the other side of the at least one second hole in the middle row being less than half the number of first holes in any of the other rows thereby defining an output waveguide;
   a light source disposed adjacent to the input waveguide; and
   a detector disposed adjacent to the output waveguide;
   wherein the at least one second hole is spaced from each of the input waveguide and the output waveguide by some of the first holes; the input waveguide, the output waveguide, a center of the at least one second hole and centers of more than one of the plurality of first holes are arranged in a line, and the at least one second hole is located at a middle of the line;
   wherein all of the first holes have the same diameter.

2. The refractive-index sensor of claim 1, wherein the first holes are arranged in an array of m rows, each of which has n holes, and each of m and n ranges from 14 to 18.

3. The refractive-index sensor of claim 1, wherein each three adjacent first holes in any two adjacent rows of the first holes are arranged in a triangle.

4. The refractive-index sensor of claim 1, wherein at least one of the first holes and the at least one second hole is cylindrical.

5. The refractive-index sensor of claim 1, wherein the photonic crystal layer is made of material selected from the group consisting of Si, GaAs and GaAlAs.

6. The refractive-index sensor of claim 1, wherein a diameter of the first holes is in an approximate range from 0.3a to 0.5a, where 'a' is a lattice constant of the photonic crystal layer.

7. The refractive-index sensor of claim 1, wherein the diameter of the at least one second hole is in an approximately range from 0.5a to 0.6a, where 'a' is a lattice constant of the photonic crystal layer.

8. The refractive-index sensor of claim 1, wherein the light source is selected form the group consisting of a light-emitting diode and a laser diode.

* * * * *